United States Patent [19]

Ushikubo

[11] Patent Number: 4,515,286

[45] Date of Patent: May 7, 1985

[54] CAP AND A CAP OPENING AND CLOSING DEVICE

[75] Inventor: Masao Ushikubo, Hachioji, Japan

[73] Assignee: Olympus Optical Co., Ltd., Japan

[21] Appl. No.: 563,070

[22] Filed: Dec. 19, 1983

[30] Foreign Application Priority Data

Dec. 22, 1982 [JP] Japan .......................... 57-194699[U]
Dec. 22, 1982 [JP] Japan .......................... 57-194700[U]

[51] Int. Cl.³ ............................................ B65D 45/28
[52] U.S. Cl. .................................................... 220/314
[58] Field of Search ................... 215/DIG. 1; 220/314

[56] References Cited

U.S. PATENT DOCUMENTS 3,215,297 11/1965 Acton et al. .................. 215/DIG. 1
4,089,463 5/1978 Babiol ........................... 215/DIG. 1

Primary Examiner—George T. Hall
Attorney, Agent, or Firm—Parkhurst & Oliff

[57] ABSTRACT

A cap and a cap opening and closing device of a liquid container for preventing a liquid evaporation is disclosed. The cap has a plurality of projections made of an elastic material on its bottom surface. The cap opening and closing device which is used in combination with the known cap or the cap mentioned above, having a shutter mechanism connected to the cap for moving the cap in cap opening and closing directions, includes a connecting member for connecting the shutter mechanism with the cap at a position remote from a center of the cap and a contact member for bringing the shutter mechanism into contact with the cap at the center of the cap, when the shutter mechanism is moved in the cap closing direction. Therefore, an easy cap opening and a complete cap closing operation can be effectively performed.

12 Claims, 17 Drawing Figures

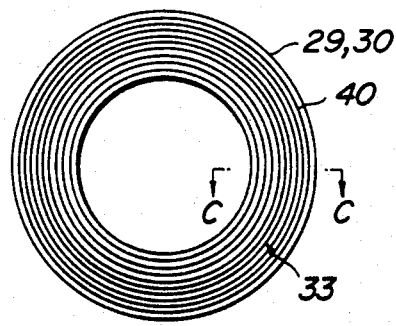
FIG_6
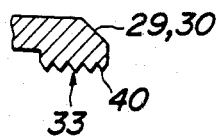
FIG_7
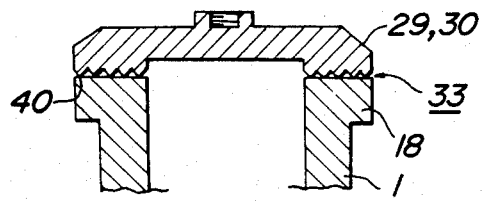
FIG_8
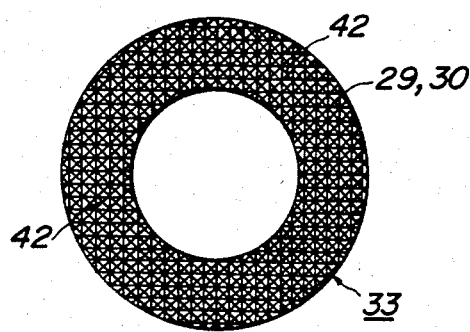
FIG_9
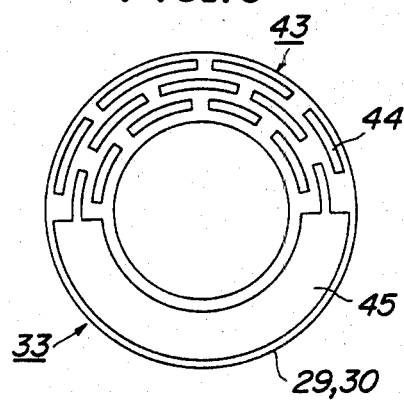
FIG_10

CAP AND A CAP OPENING AND CLOSING DEVICE

BACKGROUND OF THE INVENTION

The present invention relates to a cap of a liquid container such as a reagent container for use in a biochemistry analyzer and also to a device for opening and closing the cap.

Heretofore, there have been proposed various caps for liquid containers, as well as cap opening and closing devices. For example, as shown in FIG. 1, multiple pairs of liquid containers 1 are arranged on a container table 2 and a pair of caps can be simultaneously opened and closed by means of a cap opening and closing device secured to a disc plate 4. FIGS. 2A to 2C are plan, front and side views, respectively, showing one embodiment of a known cap opening and closing device. In those figures, a shutter 6 is arranged rotatably about a shaft 5 secured to the disc plate 4 and is energized in the direction of arrow A as shown in FIG. 2C by means of a spring 7 arranged around the shaft 5. A center portion of the shutter 6 is coupled with a leaf spring 9 by means of a connecting member 8. Both end portions 10, 11 of the leaf spring 9 are respectively connected to caps 14, 15 by means of connecting means 12, 13. Moreover, the shutter 6 has an arm portion 16 extending on an opposite side with respect to the caps 14, 15, and, as shown in FIG. 2C, a press member 17 is arranged to move forward and backward in the directions indicated by double headed arrows B and C by means of a drive means not show. Therefore, when the arm portion 16 is pressed by moving the press member 17 in the arrow B direction, the caps 14 and 15 can be removed from the liquid containers 1 by rotating the shutter 6 in an anti-clockwise direction about the shaft 5 against a force of the spring 7. When the press member 17 is moved in the arrow C direction, the caps 14 and 15 can be returned to an original position by means of the force of the spring 7. In this manner, cap opening and closing operations can be controlled by moving the press member 17 in the arrow B or C direction.

However, in the embodiment mentioned above, circular caps 14 and 15 are connected at the respective center portions thereof to the leaf spring 9 through the connecting means 12 and 13, and the center positions of the caps 14 and 15 are made identical with those of the liquid containers 1. Therefore, when the cap is removed from an opening defined by a mouthpiece 18 of the liquid container 1, the stress applied to the cap from the leaf spring 9 is almost uniform along the circular mouthpiece 18.

Moreover, in case of freezing the liquid container under the condition such that the opening of the liquid container is closed by the cap for preventing the liquid evaporation, there occurs a drawback that an inside pressure of the liquid container becomes a negative pressure state and thus the cap is tightly secured to the liquid container. Moreover, in an extreme case, the liquid contained in the liquid container is stuck to surfaces of the cap and the container, and thus the cap is adhered to the mouthpiece 18 of the liquid container. In this case, if the stress is applied to the arm portion 16 of the shutter by moving the press member 17 in the arrow B direction so as to remove the cap from the container, it is sometimes impossible to remove the cap from the opening of the liquid container due to the negative pressure in the liquid container and an adhesive force between the cap and the liquid container.

SUMMARY OF THE INVENTION

The present invention has for its object to eliminate the drawbacks mentioned above and to provide a cap of the liquid container for preventing liquid evaporation in the liquid container which can be easily removed from the liquid container at any time.

According to the invention, a cap for airtightly closing an opening of a liquid container to prevent an evaporation of a liquid contained therein comprises a plurality of projections made of elastic material and formed in a bottom surface which is to be urged against an upper surface of a mouthpiece defining the opening of the liquid container.

Another object of the invention is to provide a cap opening and closing device of a liquid container in which a cap can be easily removed from the liquid container even if the cap is firmly adhered to a mouthpiece of the liquid container or even after freezing.

According to the invention, in a device for opening and closing a cap of a liquid container comprising a shutter mechanism connected to the cap for moving the cap in a cap opening direction and a cap closing direction, the improvement comprises a connecting means for connecting the shutter mechanism with the cap at a position remote from a center of the cap; and a contact means for bringing the shutter mechanism into contact with the cap at the center of the cap, when the shutter mechanism is moved in the cap closing direction.

BRIEF DESCRIPTION OF THE DRAWINGS

FIG. 6 is a schematic view showing one embodiment of the cap according to the invention;

FIG. 7 is a cross sectional view cut along C—C line of the embodiment shown in FIG. 6;

FIG. 8 is a cross sectional view illustrating the cap shown in FIG. 6 urged against a mouthpiece of a liquid container;

FIGS. 9 and 10 are schematic views depicting other embodiments of the cap according to the invention;

DESCRIPTION OF THE PREFERRED EMBODIMENTS

Figure 1:
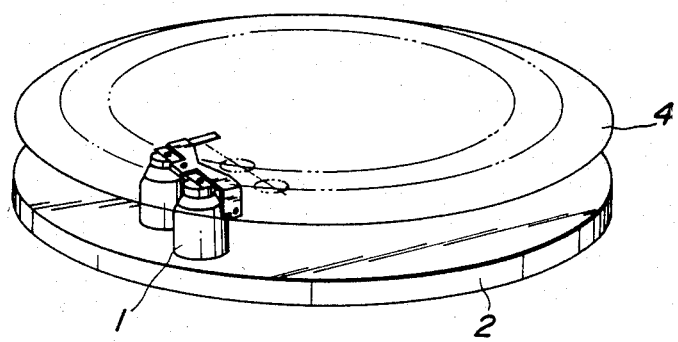
FIG. 1 is a schematic view showing one embodiment of a known cap opening and closing device.
Figure 2A:
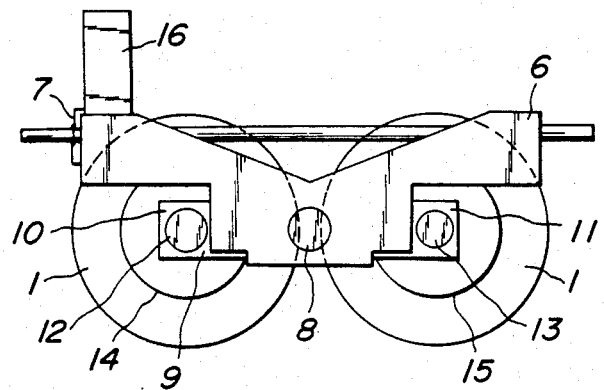
FIGS. 2A to 2C are plan, front and side views respectively illustrating the enlarged known cap opening and closing device.
Figure 2B:
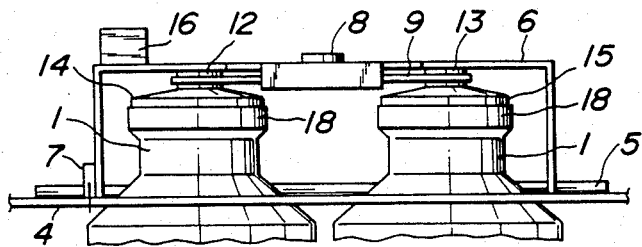
Figure 2C:
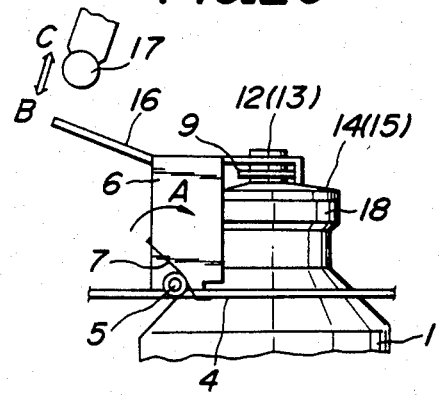
Figure 3A:
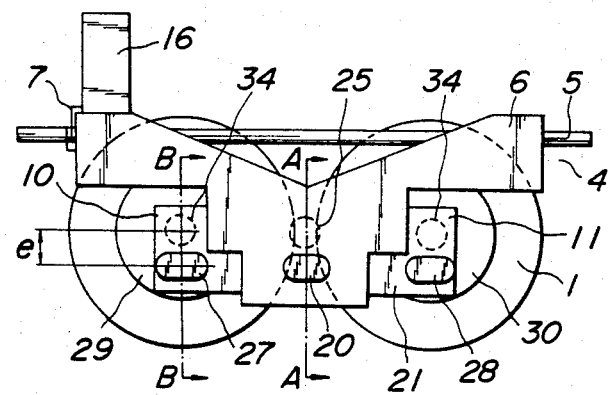
FIGS. 3A and 3B are plan and side views depicting one embodiment of the cap opening and closing device according to the invention.
Figure 3B:
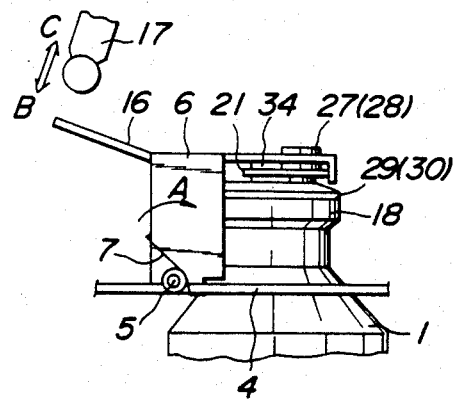
Figure 4:
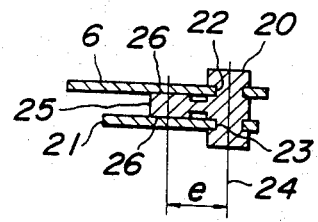
FIGS. 4 and 5 are cross sectional views respectively cut along lines A—A and B—B of the cap opening and closing device shown in FIGS. 3A and 3B.
Figure 5:
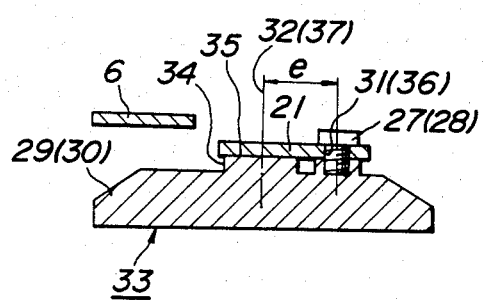

FIGS. 3A and 3B are plan and side views showing one embodiment of the cap opening and closing device according to the invention. Portions in FIGS. 3A and 3B similar to those shown in FIG. 2 are denoted by the same reference numerals used in FIG. 2, and explanations thereof are omitted here. In FIGS. 3A and 3B, a center portion of a shutter 6 is connected to a leaf spring 21 by means of a connecting means 20 having an oval cross section. This connection is performed by passing the connecting means 20 through holes 22 and 23 respectively formed in the shutter 6 and the leaf spring 21 as shown in FIG. 4 by a cross sectional view cut along the A—A line in FIG. 3A. A circular contact means 25 having a predetermined thickness is formed integrally with the connecting means 20 at a position remote from a central axis 24 of the holes 22 and 23 by a distance e. The thickness of the circular contact means 25 is arranged so as to keep a positional relation between the shutter 6 and the leaf spring 21 in parallel with each other, and the circular contact means is brought into contact with the shutter 6 and the leaf spring 21 at contact portions 26 as shown in FIG. 4. Both end portions 10 and 11 of the leaf spring 21 are respectively connected to caps 29 and 30 by means of connecting means 27 and 28 each having an oval cross section. This connection between the caps 29, 30 and the leaf spring 21 is performed by passing the connecting means 27, 28 through oval holes 31, 36 formed in the leaf spring 21 at positions remote from central axes 32, 37 of the caps 29, 30 by the distance e as shown in FIG. 5 by a cross sectional view cut along the B—B line in FIG. 3A. Moreover, a surface 33 of the caps 29, 30 opposite to the leaf spring 21 can be airtightly connected to the mouthpiece 18 of the liquid container 1. Top contact means 34 of the caps 29 and 30 is brought into contact with the leaf spring 21 at both end portions 35 thereof. Center lines connecting those of the connecting means 20, 27 and 28, and those of the contact means 25 and 34 respectively are arranged substantially parallel to the shaft 5.

In the cap opening and closing device mentioned above, as is the same as the device shown in FIG. 2, the cap opening and closing operations are performed by moving the press member 17 in the direction of double-headed arrow B or C. The cap closing operation is performed by rotating the shutter 6 about the shaft 5 in the arrow A direction by means of the elastic force of the spring 7. In this case, since the shutter 6 and the leaf spring 21 are arranged substantially parallel with each other by means of the connecting means 20, the shutter rotation force is transferred to the leaf spring 21 through both the connecting means 20 and the circular contact means 25. Then, the leaf spring 21 transfers this rotation force to the caps 29 and 30 through both end portions 10 and 11 thereof. Moreover, since the caps 29 and 30 are brought into contact with the leaf spring 21 by means of the contact means 34 as well as the connecting means 27 and 28, the shutter rotation force is transferred to the caps 29 and 30 mainly through the contact means 34 arranged at the center portion of the caps 29 and 30 in case of effecting the cap closing operation. Therefore, the caps 29 and 30 are uniformly urged against the mouthpiece 18 of the containers 1, and thus it is possible to perform the cap closing operation without causing a gap between the cap and the container. Contrary to this, in case of effecting the cap opening operation, the shutter 6 is rotated about the shaft 5 in the anti-clockwise direction by moving the press member 17 in the arrow B direction. In this case, since the shutter 6 is connected to the leaf spring 21 only by means of the connecting means 20, the contact means 25 is not brought into contact with the shutter 6 and the leaf spring 21 during the shutter opening operation, and thus the shutter rotation force is transferred to the leaf spring 21 only through the connecting means 20. Moreover, since the connecting means 27 and 28 are located in the positions remote from the center of the caps 29 and 30, the top contact means 34 is not brought into contact with the leaf spring 21 during the shutter opening operation. In this case, since the shutter rotation force is transferred to the caps 29 and 30 through the connecting means 27 and 28, the caps 29, 30 are pulled up at the position of the connecting means 27 and 28. Then the cap is locally deformed upward and thus it is possible to remove easily the cap from the opening of the container against the adhesive force between the cap and the mouthpiece and the negative pressure inside the container.

FIG. 6 is a schematic view showing one embodiment of a bottom surface of the cap according to the invention which is brought into contact with a mouthpiece of a liquid container. In this embodiment, a plurality of concentrically circular grooves 40 each having a triangular cross section are formed in the bottom surface 33 of caps 29 and 30 as shown in FIG. 7 by C—C cross section in FIG. 6. When the caps 29 and 30 are connected to the mouthpieces 18 of the containers 1, it is possible to close completely the openings 18 by means of the caps 29 and 30 each having a plurality of deformed circular grooves 40, as clearly understood from a cross section shown in FIG. 8. Since the cap is made of an elastic material and the cap closing operation is performed by keeping the circular grooves in an elastically deformed state, it is possible to effect easily the cap opening operation by utilizing a recovery force of this elastic deformation as compared with the known cap. Further, in case of effecting the cap opening and closing operation, the circular grooves 40 made of elastic material are served to cause, in a microscopic view, a relative movement between the caps 29, 30 and the mouthpiece 18 of the liquid containers 1. Therefore, it is possible to prevent effectively the connection between the caps 29, 30 and the mouthpiece 18 of the openings.

FIGS. 9 and 10 are schematic views showing other embodiments of the cap according to the invention. In the embodiment shown in FIG. 9, a plurality of projections each having a pyramid shape and made of an elastic material are formed in the bottom surface 33 of the caps 29, 30. Moreover, in case of closing the openings by the caps 29 and 30, each pyramid-shaped projection 42 is elastically deformed and thus it is possible to close the opening airtightly by the caps 29 and 30. In the embodiment shown in FIG. 10, a plurality of projections 44 are formed as concentrical segments of arcs which are arranged in an interdigital manner on one half portion 43 of the bottom surface 33 to which is applied the pulling force, while on the other half portion a semicircular projection 45 is formed. In this embodiment, in case of closing the openings by the caps 29, 30 each having the bottom shape mentioned above, it is possible to preserve liquids in the containers 1 airtightly because the caps 29, 30 are hermetically connected to the mouthpieces 18 of the containers 1. In addition, in case of effecting the cap opening operation, since the airtightness is broken from the portion 43 to which the large pulling force is applied and thus the inside pressure of the container becomes identical with the outer one, it is possible to effect more easily the cap opening operation by utilizing the device mentioned above together with the recovery force due to the elastic deformation and the relative movement between the cap and the opening.

Figure 11A:
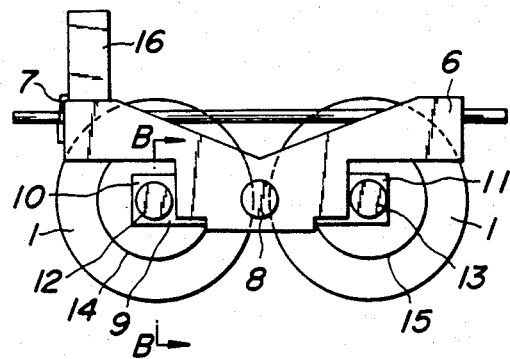
FIGS. 11A and 12A are plan views showing embodiments of the cap according to the invention and A cap opening and closing device.
Figure 11B:
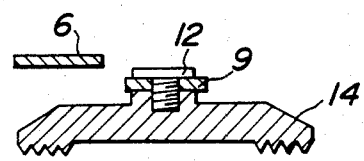
FIGS. 11B and 12B are cross sectional views respectively cut along A—A line of the embodiments shown in FIGS. 11A and 12A.
Figure 12A:
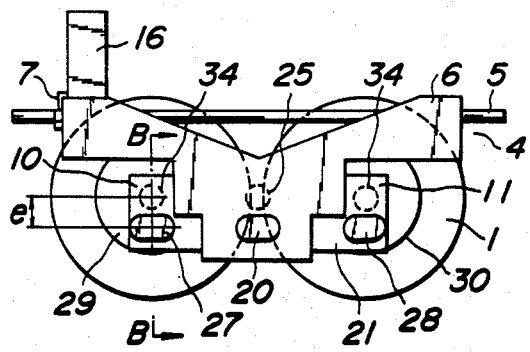
Figure 12B:
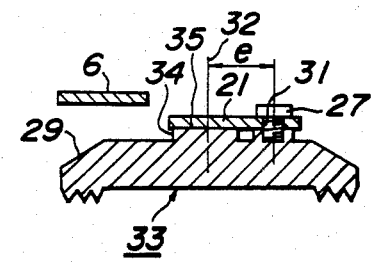

The cap mentioned above may be used with the known cap opening and closing device shown in FIG. 2, but the cap mentioned above can be effectively utilized with the cap opening and closing device shown in FIGS. 3A and 3B according to the invention. FIGS. 11A and 11B show an embodiment such that the cap mentioned above is used with the known cap opening and closing device, while FIGS. 12A and 12B illustrate an embodiment such that the cap is used with the cap opening and closing device according to the invention. Items in FIGS. 11A, 11B, 12A and 12B similar to those shown in FIGS. 2A, 2B, 2C, 3A and 3B are denoted by the same reference numerals used in FIGS. 2A to 3B, and the explanations thereof are omitted here. In these embodiments, it is a matter of course that the combination of the cap and the device shown in FIGS. 12A and 12B is more effective than that with the conventional device shown in FIGS. 11A and 11B.

As mentioned above, according to the cap and the cap opening and closing device of the present invention, since the contact means through which a cap closing force is applied to the cap is arranged at a center of the cap, while the connecting means through which a cap opening force is applied to the cap is arranged at a position remote from the center of the cap, the cap closing operation can be performed by applying uniformly the cap closing force to the mouthpiece of the opening of the liquid container without causing a gap, while the cap opening operation can be easily performed by pulling the cap at the portion remote from the center. Further, since the various projections are formed in a bottom surface of the cap made of an elastic material, an easy cap opening operation and a complete cap closing operation can be performed due to the deformation of the cap according to the invention.

What is claimed is:

1. A cap for sealing airtightly an opening of a liquid container to prevent evaporation of a liquid contained therein, comprising a plurality of projections formed in a bottom surface of the cap which is to be urged against a upper surface of a mouthpiece defining the opening of a liquid container, said projections comprising an elastic material such that said projections are elastically deformable to airtightly seal said opening and such that a force employed to so elastically deform said projections can be substantially recovered to aid in breaking said seal when said cap is removed from said mouthpiece.

2. A cap according to claim 1, wherein the cap is wholly made of said elastic material and said projections are integrally formed with the bottom surface of the cap.

3. A cap according to claim 1, wherein each said projection is formed by a concentrically circular groove having a triangular cross section.

4. A cap according to claim 1, wherein each said projection has a pyramid shape.

5. A cap according to claim 1, wherein said of said projections are formed as segments of concentric arcs and are arranged in an interdigital manner.

6. A cap according to claim 5, wherein one projection is formed by a semicircular segment having a large width.

7. In a device for opening and closing a cap of a liquid container comprising a shutter mechanism connected to the cap for moving the cap in a cap opening direction and a cap closing direction, the improvement comprising
a connecting means for connecting the shutter mechanism with the cap at a position remote from a center of the cap; and
a contact means for bringing the shutter mechanism into contact with the cap at the center of the cap, when the shutter mechanism is moved in the cap closing direction.

8. A device according to claim 7, wherein said shutter mechanism comprises a shaft extending horizontally, a shutter arranged rotatably about the shaft, a spring arranged around the shaft for biasing the shutter rotatably in the cap closing direction, and arm connected to the shutter and extending in an opposite side to the cap with respect to the shaft, and a leaf spring coupled with the shutter, said leaf spring being connected to the cap.

9. A deivce according to claim 8, wherein said leaf spring is coupled with two caps of two liquid containers arranged side by side and said shutter is coupled with the leaf spring at its center between the caps.

10. A device according to claim 9, wherein the shutter is connected to the leaf spring at a position which is deviated from a line connecting the centers of the caps on a side on which the connecting means for connecting the leaf spring to the caps situate.

11. A device according to claim 10, wherein the shutter mechanism further comprises a second contact means for urging the shutter against the leaf spring at its center situating above said connecting line when the shutter is rotated in the cap closing direction.

12. A combination of a cap of a liquid container and a cap opening and closing device, the cap comprising a plurality of projections made of elastic material and formed in a bottom surface which is to be urged against an upper surface of a mouthpiece defining the opening of the liquid container and the cap opening and closing device comprising a shutter mechanism connected to the cap for moving the cap in a cap opening direction and a cap closing direction, a connecting means for connecting the shutter mechanism with the cap at a position remote from a center of the cap, and a contact means for bringing the shutter mechanism into contact with the cap at the center of the cap, when the shutter mechanism is moved in the cap closing direction.

* * * * *